US011103522B2

(12) United States Patent
Kneller

(10) Patent No.: US 11,103,522 B2
(45) Date of Patent: Aug. 31, 2021

(54) PALATINOSE FOR ENHANCING DIETARY SUPPLEMENT AND PHARMACEUTICAL DELIVERY

(71) Applicant: Bruce W. Kneller, Howell, NJ (US)

(72) Inventor: Bruce W. Kneller, Howell, NJ (US)

( * ) Notice: Subject to any disclaimer, the term of this patent is extended or adjusted under 35 U.S.C. 154(b) by 0 days.

(21) Appl. No.: 16/785,498

(22) Filed: Feb. 7, 2020

(65) Prior Publication Data
US 2020/0237791 A1    Jul. 30, 2020

Related U.S. Application Data

(63) Continuation of application No. 15/666,528, filed on Aug. 1, 2017, now Pat. No. 10,624,915, which is a continuation of application No. 13/351,747, filed on Jan. 17, 2012, now abandoned, which is a continuation of application No. 12/410,861, filed on Mar. 25, 2009, now abandoned, which is a continuation of application No. 11/385,137, filed on Mar. 20, 2006, now Pat. No. 8,283,327.

(60) Provisional application No. 60/663,384, filed on Mar. 19, 2005.

(51) Int. Cl.
| A61K 31/7016 | (2006.01) |
| A61K 9/00 | (2006.01) |
| A61K 31/122 | (2006.01) |
| A61K 31/197 | (2006.01) |
| A61K 31/566 | (2006.01) |
| A61K 31/70 | (2006.01) |
| A61K 31/7076 | (2006.01) |
| A61K 33/00 | (2006.01) |
| A61K 38/05 | (2006.01) |
| A61K 45/06 | (2006.01) |

(52) U.S. Cl.
CPC ........ *A61K 31/7016* (2013.01); *A61K 9/0019* (2013.01); *A61K 31/122* (2013.01); *A61K 31/197* (2013.01); *A61K 31/566* (2013.01); *A61K 31/70* (2013.01); *A61K 31/7076* (2013.01); *A61K 33/00* (2013.01); *A61K 38/05* (2013.01); *A61K 45/06* (2013.01)

(58) Field of Classification Search
CPC .............. A61K 31/7016; A61K 31/197; A61K 9/0019; A61K 31/122; A61K 31/566; A61K 31/70; A61K 31/7076; A61K 33/00; A61K 38/05; A61K 45/06
See application file for complete search history.

(56) References Cited

U.S. PATENT DOCUMENTS

| 4,948,616 A | 8/1990 | Iijima et al. |
| 5,156,866 A | 10/1992 | Sato et al. |
| 5,378,131 A | 1/1995 | Greenberg |
| 5,614,224 A | 3/1997 | Womack |
| 5,659,028 A | 8/1997 | Coussement et al. |
| 5,968,544 A | 10/1999 | Howard et al. |
| 6,248,378 B1 | 6/2001 | Ganan-Calvo |
| 6,297,281 B1 | 10/2001 | Chabrier de Lassauniere et al. |
| 6,444,241 B1 | 9/2002 | Tyrpin et al. |
| 6,652,901 B2 | 11/2003 | Ishii |
| 6,713,116 B1 | 3/2004 | Aldrich et al. |
| 6,750,331 B1 | 6/2004 | Takaichi et al. |
| 10,626,915 B2 | 4/2020 | Kneller |
| 2002/0193342 A1 | 12/2002 | Hamman |
| 2003/0143311 A1 | 7/2003 | Gillota |
| 2003/0219500 A1 | 11/2003 | Howard et al. |
| 2004/0047921 A1 | 3/2004 | Simmons et al. |
| 2004/0058033 A1 | 3/2004 | Sozzi et al. |
| 2004/0132670 A1 | 7/2004 | Kowalczyk et al. |
| 2004/0241256 A1 | 12/2004 | Ehrenpreis |
| 2005/0002988 A1 | 1/2005 | Mizumoto et al. |
| 2006/0051456 A1 | 3/2006 | Kabse et al. |
| 2006/0153899 A1 | 7/2006 | Kneller |
| 2006/0188627 A1 | 8/2006 | Brouns et al. |
| 2006/0292134 A1 | 12/2006 | Stohs |
| 2007/0116801 A1 | 5/2007 | Kowalczyk et al. |
| 2007/0224265 A1 | 9/2007 | Hara et al. |
| 2008/0193603 A1 | 8/2008 | Hayes et al. |
| 2009/0181922 A1 | 7/2009 | Kneller |
| 2009/0281055 A1 | 11/2009 | Kneller |
| 2012/0183671 A1 | 7/2012 | Kneller |
| 2013/0095125 A1 | 4/2013 | Kneller |

FOREIGN PATENT DOCUMENTS

| EP | 0390438 A1 | 10/1990 |
| JP | 64-60360 | 3/1989 |

(Continued)

OTHER PUBLICATIONS

Arcot et al., RIRDC Publication No. 05/027, Mar. 2005, 35 pages. (Year: 2005).*

(Continued)

*Primary Examiner* — Jonathan S Lau
(74) *Attorney, Agent, or Firm* — Morse, Barnes-Brown & Pendleton, P.C.; Stanley F. Chalvire, Esq.; Lisa M. Warren, Esq.

(57) ABSTRACT

The present invention is directed to a dietary supplement comprising palatinose or a derivative thereof. The dietary supplement may be a nutritional product, a sports performance product, a weight loss product or a meal replacement product. The present invention is also directed to a method of increasing the absorption of a compound into the bloodstream, cells and tissue comprising administering palatinose, or a derivative thereof, in combination with the compound. The present invention also relates to a diluent for parenteral compounds. The diluent comprises palatinose or a derivative thereof. Another aspect of the present invention is directed to a method of decreasing the recovery time to pre-performance levels of total adenosine triphosphate (ATP) levels in a mammal comprising administering palatinose, or a derivative thereof, to the mammal. The present invention is further directed to a method of supplying a compound to a diabetic patient, burn victim patient or trauma victim patient. The method comprises administering palatinose, or a derivative thereof, in combination with the compound.

12 Claims, No Drawings

(56) References Cited

FOREIGN PATENT DOCUMENTS

| | | | |
|---|---|---|---|
| JP | 2001169752 A * | 6/2001 | |
| JP | 2001-187736 | 7/2001 | |
| KR | 20040092232 A | 11/2004 | |
| WO | WO 2003/022288 A1 | 3/2003 | |
| WO | WO 2004/082674 A1 | 9/2004 | |
| WO | WO 2005/061690 A1 | 7/2005 | |

OTHER PUBLICATIONS

Arai, et al., "Effects of a Palatinose-Based Liquid Diet (Inslow) on Glycemic Control and the Second-Meal Effect in Healthy Men," *Metabolism Clinical and Experimental*, 56:115-121, (2007).
Arenas, et al. "Carnitine in Muscle, Serum, and Urine of Nonprofessional Athletes: Effects of Physical Exercise, Training, and L-Carnitine Administration," *Muscle & Nerve*, 14:598-604, (1991).
Bowen, "Absorption of Amino Acids and Peptides," Colorado State University, Jul. 8, 2006. Web. Jan. 21, 2015. <http://www.vivo.colostate.edu/hbooks/pathphys/digestion/smallgut/absorb_aacids.html>.
Curran, et al., "Kinetic Relations of the Na-Amino Acid Interaction at the Mucosal Border of Intestine," *J. Gen. Physiol.*, 50:1261-1286, (1967).
Eijinde, et al., "Effect of Oral Creatine Supplementation on Human Muscle GLUT 4 Protein Content After Immobilization," *Diabetes*, 50:18-23, (2001).
Fernie, et al., "The Sucrose Analog Palatinose Leads to a Stimulation of Sucrose Degradation and Starch Synthesis When Supplied to Discs of Growing Potato Tubers," *Plany Physiology*, 125:1967-1977, (2001).
Gaby, "The Role of Coenzyme $Q_{10}$ in Clinical Medicine: Part I," *Alt Med Rev*, 1:11-17, (1996).
Gerstner, "How to Fortify Beverages with Calcium," *Food Marketing & Technology*, pp. 16-19, (Oct. 2003).
Hodgson, et al., "Coenzyme Q10 Improves Blood Pressure and Glycemic Control: A Controlled Trial in Subjects with Type 2 Diabetes," *Eur. J. Clin. Nutr.*, 56:1137-1142, (2002).
Kawai, et al. "Changes in Blood Glucose and Insulin After an Oral Palatinose Administration in Normal Subjects," *Endocrinologia Japonica*, 32(6):933-936, (1985).
Krastanova, et al. "Production of Palatinose Using Serratia Plymuthica Cells Immobilized in Chitosan," *Journal of Industrial Microbiology and Biotechnology*, 30:593-598, (2003).
Lucke, et al., "Amino Acid Transport in Brush-Border-Membrane Vesicles Isolated from Human Small Intestine," *Biochem. J.*, 168:529-532, (1977).
Magkos, et al., "Caffeine and Ephedrine: Physiological, Metabolic and Performance-Enhancing Effects," *Sports Med*, 34(13):871-888, (2004).
Meissner, "New Energy Profiles for Sports Drinks. Sachon-Fachzeitschriftenarchiv," fzarchiv.sachon.de BBII:56-57, (2006). Retrieved on-line Dec. 20, 2010.
Mingrone, et al., "L-Carnitine Improves Glucose Disposal in Type 2 Diabetic Patients," *J. Am. Coll. Nutr.*, 18:77-82, (1999).
Oizumi, et al., "A Palatinose-Based Balanced Formula Improves Glucose Tolerance, Serum Free Fatty Acid Levels and Body Fat Composition," *Tohoku J Exp Med.*, 212:91-99, (2007).
Salazar-Martinez, et al., "Coffee Consumption and Risk for Type 2 Diabetes Mellitus," *Ann. Intern Med.*, 140:1-8, (2004).
Suzuki, et al., "Effects of Dietary Palatinose and Reduced-Palatinose on Body Energy Composition," *J. Clin. Biochem. Nutr.*, 13:117-125, (1992).
Dirienzo, D., Nutritional Properties of Milk Powders, Milk Protein Concentrates and Milk Protein Isolates in *Reference Manual for U.S. Milk Powders and Microfiltered Ingredients*, Arlington, VA: U.S. Dairy Export Counsil, pp. 67-95 (Jan. 2019).
Lindmark-Mansson, et al., Int. Dairy J., 2003, 13, p. 409-425. (Year: 2003).
Bendahan, et al., Br. J. Sports Med., 2002, 36, p. 282-289. (Year: 2002).
Final Office Action for U.S. Appl. No. 11/385,137, dated Apr. 16, 2009.
Final Office Action for U.S. Appl. No. 11/385,137, dated Jun. 14, 2011.
Final Office Action for U.S. Appl. No. 13/351,747, dated Jun. 29, 2015.
Final Office Action for U.S. Appl. No. 13/351,747, dated Oct. 31, 2016.
Final Office Action for U.S. Appl. No. 13/709,763, dated Jan. 19, 2016.
Non-Final Office Action for U.S. Appl. No. 11/385,137, dated Sep. 19, 2008.
Non-Final Office Action for U.S. Appl. No. 11/385,137, dated Nov. 19, 2010.
Non-Final Office Action for U.S. Appl. No. 12/410,861, dated Dec. 2, 2010.
Non-Final Office Action for U.S. Appl. No. 12/504,480, dated May 5, 2011.
Non-Final Office Action for U.S. Appl. No. 13/351,747, dated Feb. 4, 2015.
Non-Final Office Action for U.S. Appl. No. 13/357,747, dated Feb. 16, 2016.
Non-Final Office Action for U.S. Appl. No. 13/709,763, dated Jul. 24, 2015.
Notice of Allowance for U.S. Appl. No. 11/385,137, dated Aug. 10, 2012.
Notice of Allowance for U.S. Appl. No. 15/666,528 dated Feb. 21, 2020.
Final Office Action for U.S. Appl. No. 15/666,528 dated Jul. 17, 2019.
Non-Final Office Action for U.S. Appl. No. 15/666,528 dated Oct. 16, 2018.
Chen, J., et al. "Effect of oral administration of high-dose nitric oxide donor L-arginine in men with organic erectile dysfunction: results of a double-blind, randomized, placebo-controlled study." *BJU Int* 83.3 (1999): 269-73.
Steers, William D. "Pharmacologic treatment of erectile dysfunction," *Reviews in Urology* 4.Suppl 3 (2002): p. S17-S25.
Chang, Shin S., and Joanne M. Cook. "Stability studies of stevioside and rebaudioside A in carbonated beverages." *Journal of Agricultural and Food Chemistry* 31.2 (1983): 409-412.
Xu, Jin Ze, et al. "Epimerisation of tea polyphenols in tea drinks." *Journal of the Science of Food and Agriculture* 83.15 (2003): 1617-1621.
Non-Final Office Action issued in U.S. Appl. No. 16/790,667 dated Feb. 17, 2021.
Non-Final Office Action issued in U.S. Appl. No. 16/824,140 dated Feb. 18, 2021.

\* cited by examiner

PALATINOSE FOR ENHANCING DIETARY SUPPLEMENT AND PHARMACEUTICAL DELIVERY

RELATED APPLICATIONS

This application is continuation of U.S. application Ser. No. 15/666,528, filed on Aug. 1, 2017, which is a continuation of U.S. application Ser. No. 13/351,747, filed on Jan. 17, 2012, which is a continuation of U.S. application Ser. No. 12/410,861, filed on Mar. 25, 2009, which is a continuation of U.S. application Ser. No. 11/385,137, filed on Mar. 20, 2006, which claims the benefit of U.S. Provisional Application No. 60/663,384, filed Mar. 19, 2005. The entire teachings of the above applications are incorporated herein by reference.

BACKGROUND OF THE INVENTION

1. Technical Field

The present invention relates to a disaccharide for therapeutic use. More particularly, the invention relates to the use of palatinose (6-O-alpha-D-glucopyranosyl-D-fructofuranose) to increase the efficacy of dietary supplements and pharmaceuticals.

2. Description of Related Art

Palatinose is a disaccharide consisting of d-glucose and d-fructose connected by an alpha-1,6-glycosidic linkage. It is also referred to as 6-O-alpha-D-glucopyranosyl-D-fructofuranose and as isomaltulose, and is readily produced commercially from sucrose by enzymatic rearrangement. Palatinose has a taste and appearance similar to that of sucrose. Because of the rate by which it is metabolized, it presents potential dietary and therapeutic uses.

Most sugars are rapidly absorbed after consumption. Therein, after oral administration of a significant amount of sucrose (common table sugar), blood glucose levels rise quickly. This is followed by a quick rise in insulin levels which brings the blood glucose level back down. The digestion and absorption of palatinose is unlike other sugars. It is completely digested and absorbed at a much slower speed, equivalent to about ⅕ of that for sucrose. Thus, after oral administration of palatinose, blood glucose and insulin levels rise more slowly and reach a lower maxima compared to sucrose. Because of this characteristic, palatinose is well suited as a sucrose replacement for diabetics and others with prediabetic dispositions.

Another benefit of palatinose is its non-cariogenic quality, i.e., does not promote tooth decay. It is used as a substitute for other sugars, particularly in the candy and chewing gum industry. Moreover, it is an improvement over other sugar-substitutes because it does not cause abdominal discomfort or diarrhea, a side-effect of many sugar alcohols.

Many compounds, including nutrients and dietary supplements, depend on the presence of a sugar for absorption from the gastrointestinal tract as well as for absorption from the plasma into various tissues/cells of the body. Studies have demonstrated that the performance enhancing supplement creatine is better absorbed into human skeletal muscle when taken with glucose. Certain amino acids are also more readily absorbed when administered with glucose. However, sucrose and other sugars are not ideal for use in combination with nutrient supplements. Sucrose is rapidly digested and absorbed into the blood stream. This results in a rapid rise in circulating insulin levels which quickly lowers circulating glucose levels. As a result, many compounds and nutrients administered in combination with sucrose may not be absorbed because of the short duration of the "sugar effect."

Moreover, excessive amounts of sugar can cause an increase in body fat, decreased sensitivity to insulin and tooth decay. Sugar substitutes, which are generally sugar alcohols, are also inadequate for purposes of aiding absorption. Although they are hydrolyzed and digested slowly, they often cause abdominal discomfort and diarrhea. Thus, an improved sugar is needed for use in the absorption of dietary supplement products as well as other therapeutic compounds.

SUMMARY OF THE INVENTION

The present invention solves the above-described problem by providing a dietary supplement comprising palatinose or a derivative thereof, a sugar, a stimulant, at least one amino acid or derivative thereof, and at least one mineral. The dietary supplement may be a nutritional product, a sports performance product, a weight loss product, or a meal replacement product. Palatinose enhances absorption of the dietary supplement components into the bloodstream, cells and tissue.

More particularly, the dietary supplement may comprise palatinose or a derivative thereof; amylose; glucose; a methylxanthine such as caffeine or theobromine or both; arginine or a salt, ester or chelate thereof; creatine or a salt, ester or chelate thereof; disodium adenosine triphosphate; calcium carbonate; sodium bicarbonate; and glucuronolactone. This dietary supplement formulation increases the athletic performance of a mammal during an approximately one to three hour period.

Still more particularly, the dietary supplement of the present invention may comprise palatinose or a derivative thereof; trehalose; amylose; amylopectin; L-carnosine; calcium carbonate; sodium bicarbonate; sulbutiamine or fursultiamine; disodium adenosine triphosphate; orotic acid; vinpocetine or *Rhodiola rosea*; and cellulose or another undigestible bulk forming starch. This dietary supplement formulation increases the athletic performance of a mammal during an approximately three to eight hour period.

Another aspect of the present invention is directed to a method of increasing the absorption of a compound into the bloodstream, cells and tissue. The method includes administering palatinose or a derivative thereof in combination with the compound.

More particularly, the compound may be a dietary supplement, a nutrient, a pharmaceutical, or a vaccine. If the compound is a dietary supplement formulation, the method may comprise adding palatinose or a derivative thereof to the dietary supplement formulation prior to administration. If the compound is a pharmaceutical formulation, the method may comprise adding palatinose or a derivative thereof to the pharmaceutical formulation.

Still, another aspect of the present invention is directed to a diluent for parenteral compounds, wherein the diluent comprises palatinose or a derivative thereof. The parenteral compound may be a dietary supplement, a nutrient, a pharmaceutical, or it vaccine.

Yet, another aspect of the present invention is directed to a method of decreasing recovery time to pre-performance levels of total adenosine triphosphate (ATP) levels in a mammal comprising administering palatinose, or derivative thereof, to the mammal. The palatinose or derivative thereof may be administered orally or parenterally. Preferably, the palatinose or derivative thereof is administered in a dose between about 0.5 grams and about 200 grams.

The present invention is also directed to a method of supplying a compound to a diabetic patient, burn victim patient or trauma victim patient. The method includes administering palatinose, or a derivative thereof, in combination with the compound. The compound may be a nutrient, dietary supplement, or pharmaceutical. The compound and palatinose or derivative thereof, may be administered orally or parenterally. In addition, the palatinose or derivative thereof is preferably administered in a dose between about 0.5 grams and about 200 grams.

Other features and advantages of the present invention will become apparent upon reading the following detailed description of embodiments of the invention, when taken in conjunction with the appended claims.

DETAILED DESCRIPTION

Studies have demonstrated that the presence of sugar directly enhances nutrient absorption into various tissues and cells. For example, a mixture of arginine and glucose is more efficiently absorbed into the vascular endothelium than arginine alone. Other studies have shown that nutrients and ergogenic sports performance products depend on the indirect presence of sugar for absorption wherein increased levels of insulin enhance the absorption of nutrients into the tissues and cells.

Palatinose offers an improvement over other sugars, including glucose, in that it is metabolized much slower by the gastrointestinal tract thereby extending the time that the "sugar effect," both direct and indirect, can have on the absorption of dietary supplements, nutrients, pharmaceuticals or vaccines. Rather than enter the blood stream, rapidly rise and fall, palatinose leads to gradual increases and sustained levels a glucose and insulin. This allows greater time and opportunity for the absorption of various compounds. With respect to dietary supplements, the end result may be greater energy, alertness, athletic performance and/or muscle development Moreover, replacing common sugars with palatinose presents other advantages. Preventing surges in blood glucose and insulin levels may help in the management and prevention of obesity, diabetes and cardiovascular disease. Recent studies have also provided evidence that palatinose may also have a positive effect on mental concentration. And unlike other sugars, palatinose does not promote tooth decay.

The Dietary Supplement Health and Education Act of 1994, commonly referred to as DSHEA, defines "dietary supplement" as any product (except tobacco) that contains at least one of the following: (1) a vitamin, (2) a mineral, (3) an herb or botanical, (4) an amino acid, (5) a dietary substance "for use to supplement the diet by increasing total dietary intake," or (6) any concentrate, metabolite, constituent, extract, or combination of any of the aforementioned ingredients. Examples of dietary supplements include, but are not limited to nutritional products; sports performance products, including ergogenic sports performing products; weight loss products; and meal replacement products. Dietary supplements may exist in various forms, including, but not limited to tablets, capsules, caplets, powders, drinks including shakes, solid food items including snack bars, etc.

In one embodiment, the dietary supplement of the present invention includes palatinose or a derivative thereof, a sugar, a stimulant, at least one amino acid or derivative thereof, and at least one mineral. For example, a dietary supplement designed to increase the athletic performance of a mammal during a one to three hour sports activity period, preferably comprises palatinose or a derivative thereof; amylose; glucose; a methylxanthine such as caffeine or theobromine or both; arginine or a salt, ester or chelate thereof; creatine or a salt, ester or chelate thereof; disodium adenosine triphosphate; calcium carbonate; sodium bicarbonate; and glucuronolactone.

Alternatively, the dietary supplement of the present invention may comprise palatinose or a derivative thereof; trehalose; amylose; amylopectin; L-carnosine; calcium carbonate; sodium bicarbonate; sulbutiamine or fursultiamine; disodium adenosine phosphate; orotic acid; vinpucetine or *Rhodiola rosea*; cellulose or another undigestible bulk forming starch; and perhaps at least one B vitamin. This dietary supplement formulation increases the athletic performance of a mammal during an approximately three to eight hour period.

Other preferred dietary supplement formulations of the present invention may comprise palatinose or a derivative thereof, and any or all of the following: water; carbon dioxide; creatine or a salt, ester or chelate thereof; carnitine or a salt, ester or chelate thereof; taurine or a salt, ester or chelate thereof; arginine or a salt, ester or chelate thereof; citrulline or a salt, ester or chelate thereof; carnosine or a salt, ester or chelate thereof; pyruvate or a salt, ester or chelate thereof; ribose; amylase; amylopectin; tyrosine or a salt, ester or chelate thereof; tyramine or a salt, ester or chelate thereof; histidine or a salt, ester or chelate thereof; alanine or a salt, ester or chelate thereof; phenylalanine or a salt, ester or chelate thereof; adenosine mono, di or triphosphate, or a salt, ester or chelate thereof; alpha lipoic acid, or a salt, ester or chelate thereof; 4-hydroxy-isoleucine; d-pinitol; ornithine or a salt, ester or chelate thereof; sodium or any salt thereof; potassium or any salt thereof; zinc or any salt thereof; magnesium or any salt thereof; iron or any salt thereof; chromium or any salt thereof; calcium or any salt thereof; vitamin B-1; vitamin B-2; vitamin B-3; vitamin B-6; vitamin B-12; pantothenic acid; folic acid; vitamin C; 7-keto-DHEA, or any ester or ether thereof; 7-hydroxy-DHEA or any ester thereof; caffeine; octopamine; norsynephrine; synephrine; ephedrine; hordenine; theobromine; evodiamine; phenylephrine; insulin; metformin; corosolic acid; glucuronolactone; ginger; ginseng; ginko biloba; *Rhodiola rosea*; fenugreek; epicatechin; epicatechin-3-gallate; epigallocatechin; epigallocatecin-3-gallate, glutamine, branched chain amino acids or any salts or esters thereof; any chelate of any amino acid; 6-methyluracil; phosphocreatinine; orotic acid; 5-hydroxytryptophan; vinpocetine; sucralose; fructose; galactose; maltodextrin; glucose; DMAE; DMG; TMG; coenzyme Q-10, sulbutiamine; fursultiamine; octotiamine; adrafanil; choline; phosphatidylcholine; and phosphatidylserine.

Due to the presence of palatinose, or derivative thereof, in the dietary supplements of the present invention, these dietary supplements increase athletic performance, energy, strength, percent fat-free muscle mass, muscle development, mental concentration and alertness, and stamina in mammals.

It should be understood that palatinose may be added to any dietary supplement formulation to enhance the effects of and improve the absorption of the dietary supplement, and the present invention is intended to encompass such improved formulations. It should also be understood that use of the palatinose in any of the embodiments or methods of the present invention may be substituted by any derivative of palatinose.

Preferably, the concentration of palatinose, or derivative thereof, in the dietary supplement is between approximately 1% and approximately 85%. More preferably, the concentration of palatinose in the dietary supplement is between approximately 10% and approximately 50%. Furthermore, the palatinose present in the dietary supplement is desirably administered in a close between about 0.5 grams and about 200 grams.

The present invention is also related to a method of increasing the absorption of a compound into the bloodstream, cells and tissue by administering palatinose, or a derivative thereof, in combination with the compound. Palatinose may be used to increase the absorption of any compound in the method of the present invention, including compounds used to treat any disease or illness. Exemplary compounds for use in the present invention include, but are not limited to a dietary supplement, a nutrient, a pharmaceutical, or a vaccine. When palatinose is used to increase the absorption of particular compounds, including dietary supplements and nutrients, the fatigue associated with an athletic performance of a mammal is reduced.

In addition, because palatinose maintains a more constant elevation of blood sugar levels as opposed to other sugars, an optimal maximum rate of adenosine triphosphate (ATP) synthesis in cells can be maintained for several hours. Most sugars, including glucose, peak in the plasma about 45 to 60 minutes post absorption and then an insulin spike drives this level down rapidly, leading to pre-prandial (or lower) levels of plasma sugar. When the plasma sugar levels decrease, ATP synthesis also decreases. Palatinose maintains a slightly heightened plasma sugar level for a longer period of time. As a result, mitochondria have access to optimal levels of carbohydrates for approximately 6 to 8 hours, thereby allowing for heightened and continued ATP synthesis. Accordingly, the administration of palatinose, or a derivative thereof, to a mammal decreases the recovery time to pre-activity performance levels of total ATP in the mammal. Preferably, palatinose is administered prior to the sports performance.

The method of the present invention may include adding palatinose, or a derivative thereof, to a dietary supplement formulation, pharmaceutical formulation or vaccine formulation prior to administering the respective compounds. Preferably, the concentration of palatinose or derivative thereof, in the dietary supplement, pharmaceutical, vaccine or other formulation, is between approximately 1% and approximately 85%. More preferably, the concentration of palatinose or derivative thereof, in the dietary supplement, pharmaceutical, vaccine or other formulation, is between approximately 10% and approximately 50%. Furthermore, the palatinose, or derivative thereof, is desirably administered in a dose between about 0.5 grams and about 200 grams.

Additional examples of compounds that may be used in the method of the present invention include, but are not limited to phosphatidyserine; S-adenosyl-methionine; nicotinamide adenine dinucleotide; any cephalosporin antibiotic; any macrolide antibiotic; any aminoglycoside; antibiotic; any penicillin antibiotic; any fluroquinolone antibiotic; any tetracycline antibiotic; chloramphenicol; any protease inhibitor antiviral; any nucleoside analog antiviral; any reverse transcriptase inhibitor antiviral; any polyene or membrane active antimycotic; any azole or inhibitor of ergosterol biosynthesis antimycotics; griseofulvin; flucytosine; capsofungin; mycafungin; any pneuraminidase inhibitor antiviral; an polymerase inhibitor antiviral; any class of interferon; any class of interleukin; any type of human growth hormone; any type of insulin growth factor or insulin like growth factor; any type of anti-vascular endothelial growth factor antibodies; any alkylating agent including those used to treat cancer of any type; any antimetabolite agent including those used to treat cancer of any type; any plant alkaloid agent including those used to treat cancer of any type; doxorubicin or any salt, ester, or chelate thereof; mitoxantrone or any salt, ester or chelate thereof; bleomycin or any salt, ester, ether or chelate thereof; platinum or any salt, ester, ether or chelate thereof; paclitaxel; docetaxel; epoeitin alfa; and darboepoeitin alfa.

The compound and palatinose may be administered by any method known to those having skill in the art including, but not limited to oral and parenteral administration. The compound and palatinose may also be administered in a solution of water or saline, wherein the saline is hypotonic, hypertonic or normotonic saline. Palatinose, or a derivative thereof, may also be used as a diluent for any parenteral compound, including, but not limited to dietary supplements, nutrients, pharmaceuticals and vaccines.

Palatinose is particularly useful for supplying any compound, including nutrients and pharmaceuticals, to patients, such as diabetic, burn victim, and trauma victim patients.

It should be understood that the foregoing relates to exemplary embodiments of the invention, and that modifications may be made without departing from the spirit and scope of the invention as set forth in the following claims.

What is claimed is:

1. A method of increasing the absorption of L-leucine into the bloodstream of a mammal, wherein the method comprises administering to the mammal a composition comprising isomaltulose and L-leucine or a salt, ester or chelate thereof, wherein the composition comprises between about 0.5 grams and about 200 grams of isomaltulose.

2. The method of claim 1, wherein the composition is selected from the group consisting of a dietary supplement, a nutrient or a pharmaceutical.

3. The method of claim 1, wherein the composition is in a form selected from the group consisting of a tablet, capsule, powder or drink.

4. The method of claim 1, wherein the concentration of isomaltulose in the composition is between about 10% and about 85%.

5. The method of claim 1, wherein the concentration of isomaltulose in the composition is between about 10% and about 50%.

6. The method of claim 1, wherein the composition further comprises one or more compounds selected from the group consisting of a sugar; a stimulant; creatine or a salt, ester or chelate thereof; carnitine or a salt, ester or chelate thereof; coenzyme Q-10; 7-keto-DHEA; a mineral; an undigestible bulk-forming starch; adenosine triphosphate; carbon dioxide; trehalose; amylose; glucose; a methylxanthine; amylopectin; calcium carbonate; sodium bicarbonate; glucuronolactone; sulbutiamine; fursultiamine; orotic acid; vinpocetine; *Rhodiola rosea*; and cellulose.

7. A method of increasing athletic performance in a mammal, wherein the method comprises administering to the mammal a composition comprising isomaltulose and L-leucine or a salt, ester or chelate thereof, wherein the composition comprises between about 0.5 grams and about 200 grams of isomaltulose.

8. The method of claim 7, wherein the composition is selected from the group consisting of a dietary supplement, a nutrient or a pharmaceutical.

9. The method of claim 7, wherein the composition is in a form selected from the group consisting of a tablet, capsule, powder or drink.

10. The method of claim 7, wherein the concentration of isomaltulose in the composition is between about 10% and about 85%.

11. The method of claim 7, wherein the concentration of isomaltulose in the composition is between about 10% and about 50%.

12. The method of claim 7, wherein the composition further comprises one or more compounds selected from the group consisting of a sugar; a stimulant; creatine or a salt, ester or chelate thereof; carnitine or a salt, ester or chelate thereof; coenzyme Q-10; 7-keto-DHEA; a mineral; an undigestible bulk-forming starch; adenosine triphosphate; carbon dioxide; trehalose; amylose; glucose; a methylxanthine; amylopectin; calcium carbonate; sodium bicarbonate; glucuronolactone; sulbutiamine; fursultiamine; orotic acid; vinpocetine; *Rhodiola rosea*; and cellulose.

\* \* \* \* \*